United States Patent [19]

Malchesky et al.

[11] 4,350,156
[45] Sep. 21, 1982

[54] METHOD AND APPARATUS FOR ON-LINE FILTRATION REMOVAL OF MACROMOLECULES FROM A PHYSIOLOGICAL FLUID

[75] Inventors: Paul S. Malchesky, Painesville Township, Lake County; Yukihiko Nose, Cleveland Heights, both of Ohio

[73] Assignee: Japan Foundation for Artificial Organs, Painesville Township, Lake County, Ohio

[21] Appl. No.: 154,581

[22] Filed: May 29, 1980

[51] Int. Cl.³ .............................................. A61M 5/00
[52] U.S. Cl. ................................. 128/214 R; 210/434
[58] Field of Search ............... 128/214 R, 400, 214 B, 128/1 R; 210/434, DIG. 927, 259, 651

[56] References Cited

U.S. PATENT DOCUMENTS

| | | | |
|---|---|---|---|
| 3,579,441 | 5/1971 | Brown | 210/434 |
| 3,802,432 | 4/1974 | Djerassi | 128/214 R |
| 3,941,356 | 3/1976 | Mason | 128/400 |
| 4,103,685 | 8/1978 | Lupien | 128/214 R |
| 4,111,199 | 9/1978 | Djerassi | 128/214 R |
| 4,191,182 | 3/1980 | Popovich | 210/434 |
| 4,215,688 | 8/1980 | Terman | 128/214 R |
| 4,223,672 | 9/1980 | Terman | 128/214 R |
| 4,243,532 | 1/1981 | Tsuda | 210/434 |

OTHER PUBLICATIONS

New Zealand Medical Journal, vol. 92, No. 666, 8-2-7-1980, pp. 145-148.
Plasmapheresis Therapy of Immunologic Disease—from Cleveland Clinic Quarterly, vol. 47, No. 2, 1980, pp. 53-72.

Primary Examiner—Richard J. Johnson
Attorney, Agent, or Firm—Baldwin, Egan, Walling & Fetzer

[57] ABSTRACT

An on-line filtration system for the removal of macromolecules greater than 70,000 mol. wt. from a physiological solution, such as blood, in the therapeutic treatment of various disease states. For blood, the plasma (which contains the macromolecules) is separated continuously from the blood using a first membrane filter with a membrane porosity of nominally 0.2 to 1.0 micron. The separated plasma is then continuously filtered in a physiological temperature state or a cooled state through a second membrane filter with a membrane porosity of nominally 0.01 to 0.2 micron, which retains the macromolecules. In the cooled state, separation of the macromolecules is effected more efficiently than could be done in the non-cooled state. The treated plasma (macromolecules removed) is then reunited with the blood flow coming from the first plasma filter and returned to the patient. The blood flow and filtration processes are generally continuous. Suitable agent(s) may be added to the separated plasma to promote formation of macromolecules.

32 Claims, 4 Drawing Figures

METHOD AND APPARATUS FOR ON-LINE FILTRATION REMOVAL OF MACROMOLECULES FROM A PHYSIOLOGICAL FLUID

This invention relates to plasmapheresis and more particularly to the removal of undesirable solutes from plasma in a plasmapheresis process.

BACKGROUND OF THE INVENTION

Plasmapheresis (the removal of blood, separation of the plasma and the reinfusion of the blood cells) with or without the replacement of the patient's plasma by donor plasma, a plasma fraction, or other physiological solution, is becoming more useful in the clinical treatment of various disease states. Such disease states have in common the presence of undesirable elevated levels of plasma solutes. Such solutes (due to their increased size) cannot be effectively removed by techniques such as dialyses and hemofiltration. Therefore plasma removal with the infusion of physiological solutions is effective in depleting their concentration. Various disease states treated by plasmapheresis are as follows:

Myasthenia gravis
Glomerulonephritis
Goodpasture's syndrome
Skin diseases
    pemphigus
    herpes gestationis
Severe asthma
Immune complex diseases
    crescentic nephritis
    systemic lupus erythematosus
    Wegner's/polyarteritis
    subacute bacterial endocarditis
    cryoglobulinemia
    cutaneous vasculitis
Diabetic hypertriglyceridemia
Hypercholesterolemia
Macroglobulinemia
    Waldenstrom's syndrome
    hyperviscosity syndromes
    paraproteiniemias, myeloma
Hematological diseases
    hemolytic anemia
    red cell agglutinins
    auto-antibody lymphocytes
    thrombotic thromcocytopenia purpura
    immune thrombocytopenia
    factor VIII inhibitor
    or antibodies
Raynaud's disease and phenomenon
Renal transplantation
Rhesus incompatibility
Hepatic coma
Hypertension
Motor neurone disease
    amyotrophic lateral sclerosis
    auto polyneuropathy
Refsum's disease
Guillain-Barre syndrome
Arthritis
Removal of protein bound toxins
    poisons—methyl parathion,
    poisonous mushrooms, paraquat
    hormones—thyroid
    protein bound aluminum—dialysis dementia
Cancer
Insulin resistant diabetes While this list is not exhaustive, it exemplifies the wide range of diseases associated with biochemical abnormalities; such biochemical agents being of high molecular weight.

At present the number of cases of plasma exchange are small and in many instances without controls. The success in some cases is quite impressive.

The treatments presently being carried out by plasmapheresis may be generally grouped into two types: (1) removal of an abnormal metabolite(s) or toxin(s) and (2) treatment of a disorder of the immune system. Examples of the first type include hepatic support, hypertriglyceridemia, hypercholesterolemia, and the removal of protein or lipid bound toxins. Examples of the second type include myasthenia gravis, glomerulonephritis, macroglobulinemias, arthritis, and systemic lupus erythematosis.

While in some of the diseases there is little known concerning the correlation of the disease with the increased plasma factors, for other diseases the factor(s) is known or correlation between the increased factor and the disease state can be shown as outlined in Table 1 and Table 2 as follows.

TABLE 1
IMMUNOLOGICAL DISORDERS TREATED BY PLASMAPHERESIS

| Disease | Increased Factor(s) or Abnormality |
| --- | --- |
| *Myasthenia gravis* | Antibody specific for acetylcholine receptor |
| Renal transplant rejection | Antibody to glomerular basement membrane |
| Goodpasture's syndrome | Antibody to basement membrane of lung |
| Rhesus incompatibility | Anti-D-antibody |
| Systemic *lupus erythematosus* | DNA antibodies and immune complexes of DNA |
| Glomerulonephritis | Immune complexes or autoantibodies |
| Macroglobulinemia (Waldenstrom's syndrome) | IgM and hyperviscosity |
| *Pemphigus vulgaris* | IgG antibodies |
| Asthma bronchitis | IgE |
| Myeloma | Myeloma globulin |
| Raynaud's disease and pnenomena | Macroglobulin, increased viscosity |
| *Thrombocytopenic purpura* | Immunocomplex |
| Cancer | α-1, α-2 globulines, β-globulins, α-1-antitrypsin, ceruloplasmin, orosomucoid, haptoglobin, IgA |
| Breast cancer | Circulating immune complex |
| Polyneuropathy | Antibodies to myelin |
| Rheumatoid arthritis | "Serum factor" |
| Diabetes | Autoantibodies to insulin receptor |
| Autoimmune hemolytic anemia | Antibody to RBC |

TABLE 2
METABOLIC DISORDERS TREATED BY PLASMAPHERESIS

| Disease | Increased Factor(s) or Abnormality |
| --- | --- |
| Hepatic coma | Metabolic factors (bilirubin) |
| Refsum's disease | Phytanic acid (bound to lipoproteins) |
| Poisonings | Protein bound drug |
| Dialysis dementia | Protein bound aluminum |

TABLE 2-continued

METABOLIC DISORDERS TREATED BY PLASMAPHERESIS

| Disease | Increased Factor(s) or Abnormality |
| --- | --- |
| Hypertriglyceridemia | Triglycerides and hyperviscosity |
| Hypercholesterolemia | Cholesterol |
| Amytrophic lateral sclerosis | Cytotoxic factors, immune complexes suspected |

Listed are various diseases for which increased levels of antibodies or macromolecules exist and for which plasmapheresis has been useful by its reduction of these substances. For example, in myasthenia gravis, antibodies specific for the acetycholine receptors are elevated. Removal of these antibodies by plasmapheresis shows improvement in the patients. In macroglobulinemia, there is an increased level of gamma globulin. Reducing this level by plasmapheresis is clinically effective.

The conventional method of plasmapheresis employs a cell centrifuge involving bulky and expensive equipment which is not portable and is very costly, and carries with its potential hazards. Namely, essential plasma products are lost that are not being replenished in the substitution fluids and the potential exists for acquiring hepatitis. In addition, the effectiveness of the procedure is limited due to the limited removal that can be accomplished in discarding a limited volume. If conventional plasmapheresis were to be accepted for the treatment of many of these diseases there would be created a greater need for plasma products than could be met nationally. Obviously, to take advantage of plasmapheresis in treating these diseases, new techniques must be developed for removal of the plasma "toxins".

A major improvement would be to develop "on-line" removal systems to remove the "toxin" in question and to return the treated plasma back to the patient. The advantages are quite obvious. The recent development of membrane systems for the on-line removal of plasma from whole blood has added impetus to the development work. Extracorporeal treatment of plasma generated by either membrane plasma separators or centrifuges has been carried out by either specific or non-specific sorbents such as activated charcoal, nonionic or ionic resins and immobilized proteins, cells or tissue.

In many of the disease states multiple biochemical abnormalities exist, and due to the nature of the abnormal substances involved, multiple sorbent systems may be required. Such developments will take many years. Therefore due to the nature of the substances (larger molecular weights of generally over 100,000 daltons) or the nature of the disease state, where the specific macromolecule that is causative for the symptoms of the disease is not defined, the more general approach of removing all molecules over a specific molecular weight can be chosen. Membranes having a molecular cutoff of about 100,000 daltons are chosen as they can pass albumin thereby negating the need to infuse this plasma product as is done by the conventional plasmapheresis process.

Therefore it is an object of the invention to provide a plasmapheresis method and apparatus for removing macromolecules of predetermined size from a plasma solution.

A further object of the invention is to provide a plasmapheresis method and apparatus of the above type wherein a physiological solution is withdrawn from a patient, treated by removing macromolecules of predetermined size, and returned to the patient in a continuous process.

A further object is to remove molecules from the plasma which form a macromolecule after adding a complexing agent to the plasma.

A further object of the invention is to provide a plasmapheresis apparatus for "on-line" removal of macromolecules of predetermined size from a patient's physiological solution that is simple in construction, inexpensive to manufacture, and highly effective in operation.

Briefly the foregoing objects are accomplished by the provision of a method of removing macromolecules from a physiological solution including: securing a physiological solution stream such as blood from a patient; separating such physiological solution stream into a concentrated cellular element stream and a plasma stream containing macromolecules therein by either a centrifuge or a membrane filter; cooling such plasma stream to a temperature of between just above the freezing point of the plasma stream and 35° centigrade; filtering macromolecules of predetermined size out of the cooled plasma stream to form a filtered plasma stream; combining such filtered plasma stream and such cellular element stream to form a processed stream; heating the processed stream to body temperature; and returning the heated processed stream to the patient in a continuous operation. In such method, the cooler cools the separated stream to a temperature between about just above the freezing point of the separated stream and about 35° centigrade to cause such macromolecules to gel or precipitate. Also, a complexing agent may be added to the plasma to promote formation of macromolecules.

The invention also includes an apparatus for removing macromolecules from a patient's physiological solution such as blood including plasma separation means, such as a centrifuge or a membrane filter, for dividing a physiological solution containing macromolecules into a concentrated cellular element stream and a plasma stream, a cooler in fluid flow communication with the plasma separation means for receiving the plasma stream therefrom and cooling such plasma stream to cause the macromolecules therein to gel or precipitate, filter means such as a membrane filter in fluid flow communication with the cooling unit for receiving the cooled plasma stream therefrom and filtering such cooled plasma stream to remove macromolecules of a predetermined size therefrom, fluid flow communication means for receiving the filtered plasma stream from the filter means and for receiving the concentrated cellular element stream and combining the two last-named streams to form a processed stream for return to the patient. A pump may be employed in fluid flow communication with the plasma separation means and with the patient to pump the physiological solution from the patient to the plasma separation means. Instead of blood the physiological solution may be lympth or ascitic fluid. The cooling unit cools the separated plasma stream to a temperature of between just above the freezing point of the separated plasma stream and approximately 35° centigrade. A heater unit may be operatively secured to the fluid flow communication means at a point in such fluid flow communication means after which the filtered plasma stream and the concentrated cellular element stream are combined to heat the processed stream to approximately body temperature before it is returned to the patient. As an alternative, the filter means may be encased in the cooling unit for receiving the cooled plasma stream therefrom to further cool such cooled plasma stream.

Other objects and advantages of the invention will be apparent from the following description taken in conjunction with the drawings wherein:

BRIEF DESCRIPTION OF THE DRAWINGS

In the drawings, like numbers and letters are used to identify like and similar parts throughout the several views.

DEFINITIONS

Figure 1:
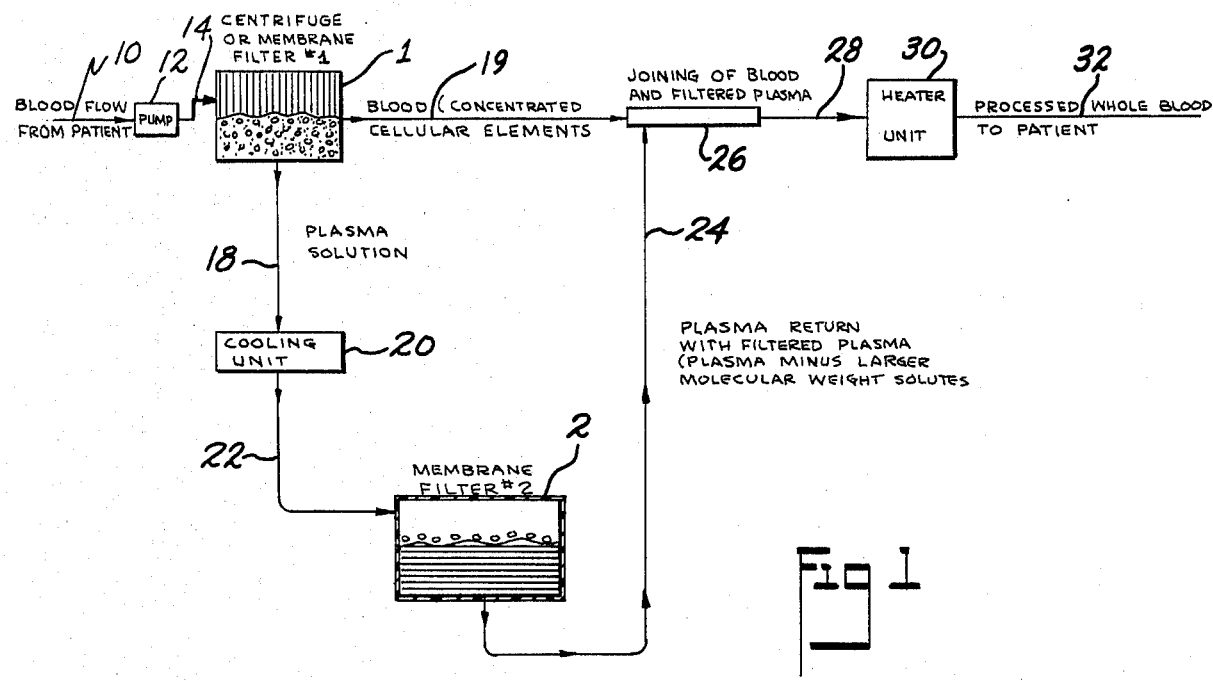
FIG. 1 is a schematic flow diagram illustrating the method and apparatus of the invention.

Cryoprecipitates: Serum globulins that precipitate or gel on cooling at low temperatures (4°–35° C.) and redissolve on warming Cryoglobulins: Homogenous proteins that have become physically altered (myeloma, mixtures of immunoglobulins (as IgG and (IgM, or immune complexes (as antigen and antibody), possible with complement (as in SLE) Mol. Wt. 100,000–1,800,000

Macromolecules: Molecules of 100,000 daltons molecular weight or higher

The use of the artificial kidney, blood oxygenators, and artificial joints is well recognized today. However, for a variety of disease states, applications of the techniques of extracorporeal circulation and mechanical or mass transfer support are becoming more recognized. Significant advances have been made in the areas of cardiac, pancreatic and liver support in recent years. Within the past decade, with the availability of the continuous flow blood cell centrifuges, many different disease states, mostly of an immunological nature, have been investigated in response to plasma exchange.

For many of the diseases, the nonspecific removal of plasma factors has correlated with improvements in the disease state. Problems with this conventional methodology in chronic applications are the limited removal related to the volume of exchange and dilution by the required infusion solution, the requirement for plasma products and the potential hazards of such infusions, and the need for bulky and expensive capital equipment. The removal of the specific plasma factors as antibodies, immune complexes, and immunoglobulins by specific agents as sorbents may be desirable; however, in most disease states the etiology is not known.

In most immunologically related disease states the presence and abnormal concentration of plasma factors greater than the molecular weight of albumin, suggests the application of membrane filtration. In practice, plasma is separated on-line from whole blood in an extracorporeal circuit. The plasma which contains the molecules of interest is then filtered through a membrane filter which rejects those macromolecules greater than albumin and allows albumin and the smaller size plasma solutes to pass and be returned to the patient. The return of the albumin obviates the requirement for infusion of large volumes of donor plasma. Such techniques are presently being applied clinically in the treatment of rheumatoid arthritis and certain other disease states.

Plasma exchange has been shown to be effective in the treatment of various diseases, including the immunologically based disease states. This technique, however, has severe limitations in chronic applications, such as limited removal related to the volume of exchange and dilution by the infusion solution and the requirement for plasma products. Removal of the macromolecules as immune complexes by specific sorbents in most cases requires extensive development work. The nonspecific removal of macromolecules by membrane filtration makes the treatment simpler and more universal in application.

In practice, plasma is separated on-line from whole blood. The plasma which contains the macromolecules is then filtered through a membrane filter which rejects the macromolecules and passes the albumin and smaller size plasma solutes which are reinfused into the patient. With rheumatoid arthritis plasma and membranes of nominal pore size of 0.1 microns, over 97% passage of albumin was achieved with greater than 25% rejection in a single pass of rheumatoid factor and Clq binding immune complexes. In certain immunologically related disease states, the increased levels of cryoprecipitates containing antigen and or antibody in the form of immune complexes with or without complement suggests that their removal could be therapeutic. Modification of the on-line plasma filtration circuit is made to include a heat exchanger to cool the plasma to below 10° C. before filtration. Using rheumatoid arthritis plasma with cryoprecipitate concentrations of greater than 5 times normal, reductions to concentrations below normal values were achieved in single pass with over 90% passage of albumin.

The techniques of on-line plasma filtration through select membranes and the cooling of plasma to promote gel formation of abnormal plasma proteins to maximize their removal are simple and easy to apply. They do not require the infusion of expensive plasma products.

Referring to the drawings, FIG. 1 illustrates the method and apparatus of the invention as applied to the filtration of blood, although it will be understood that any other type of physiological fluid such as, for example, lymph, ascitic fluid, etc., may be treated.

In FIG. 1, blood is drawn from a patient into line 10 and fed into a pump 12 from which it is pumped into a line 14 and then into membrane filter 1. In place of membrane filter 1, a centrifuge may be employed as the function at this point is to separate the blood into a plasma solution stream (fed into line 18) and a concentrated cellular element stream (which is fed into line 19).

From the membrane filter 1, the plasma solution is led down a line 18 to a cooling unit 20 where the plasma solution is cooled to a temperature of between just above the freezing point of the plasma solution and about 35° centigrade to cause the macromolecules to gel or precipitate. Next, the cooled plasma solution is led down the line 22 to membrane filter 2, where the macromolecules are retained (and the albumin and lower molecular weight components pass through).

From filter 2, the filtered plasma (plasma) minus larger molecular weight solute is led through the line 24 to the juncture 26, where the filtered plasma stream and the concentrated cellular element stream are joined or united (to form a processed stream) and then fed into line 28 and thence into the heater unit 30. The heater unit 30 heats the processed stream to body temperature. The heated processed stream is then fed into the line 32 and returned to the patient in a continuous process.

Figure 2:
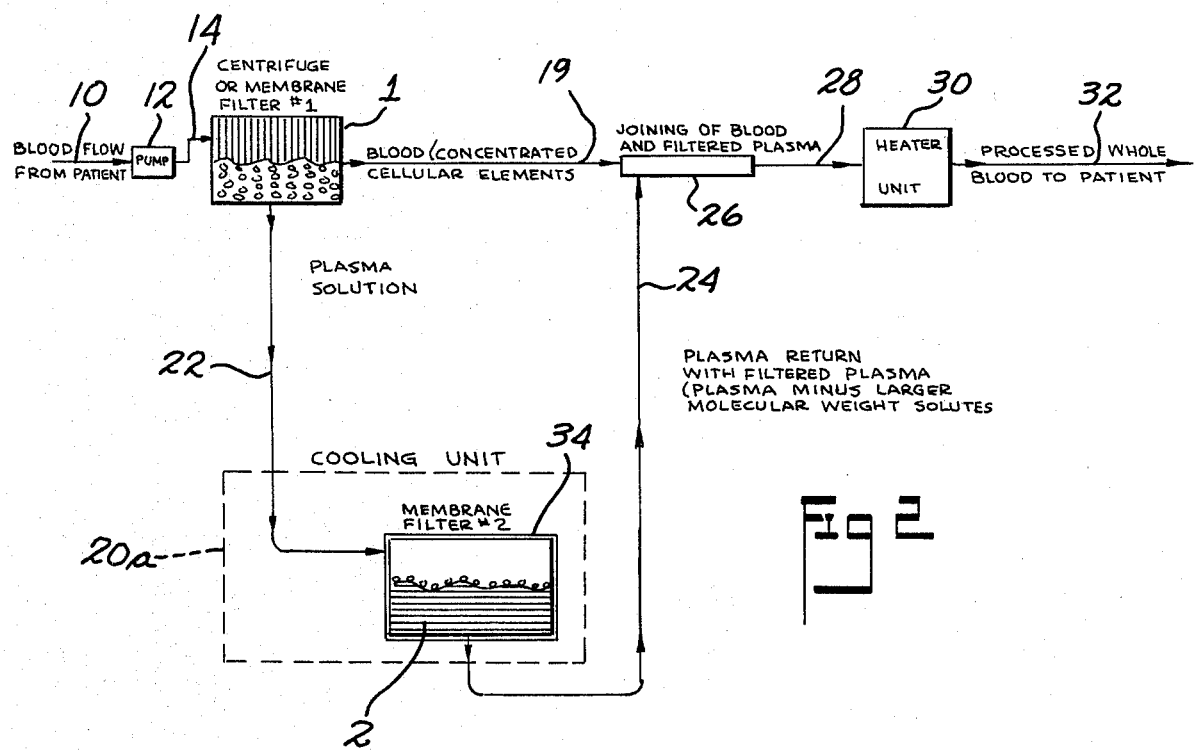
FIG. 2 is a schematic flow diagram similar to FIG. 1, but showing a modification thereof.

In the FIG. 2 modification, the cooling unit 20a is shown encasing the filter 2 (and a portion of the incoming line 22) such filter 2 being enclosed in a layer of insulation 34. This structure assures proper (cooled) temperature maintenance within filter 2 during the filtering process.

It is to be understood that, if required, it would be in order to inject into line 22 (before cooling) a complexing agent for effecting gelling or precipitation or macromolecule formation. A complexing agent is an agent which will allow single or multiple plasma factors to form a complex of higher molecular weight. Such agent could be a sorbing agent or ion exchange material such as, for example, heparin which forms complexes with cholesterol and lipid containing components.

Thus, FIGS. 1 and 2 outline filtration for the separation of plasma from whole blood. A cell centrifuge could also be used in place of membrane filter 1 for the generation of the plasma flow stream. The plasma, which contains the factors of interest, is directed to a membrane filter 2 designed to filter out the macromolecule(s) of interest, but pass those plasma solutes of smaller size. The plasma is then reunited with the blood flow (concentrated cellular element stream) from filter 1 (or in the case of a centrifuge the blood flow from the centrifuge) before being returned to the patient.

For filter 1, a membrane with a normal porosity of 0.2–1 micron would be required to generate the plasma. Past investigations with membranes in the lower range porosity have indicated that sieving coefficients of certain plasma macromolecules in the normal and the disease states are low (less than 0.8). In addition, operational conditions of filter 1, including blood and plasma flows, and velocities and transmembrane pressures may seriously affect the sieving properties of the macromolecules of interest. The filtration of blood in filter 1 is cross flow. Filter 2, which employs a membrane with a porosity of nominally 0.01 to 0.2 microns, would be required to remove macromolecules of 100,000 daltons molecular weight or greater. For this porosity, essential substances as albumin and lower molecular weight solutes will pass through the membrane filter 2 and be returned to the patient. The filtration of the plasma in this filter may be cross flow or conventional (flow directly into filtration media). In cross flow, a recirculation circuit and an additional pump are required. In tnis recirculation circuit a variable resistor (as a screw clamp) may be placed to regulate the rate of filtration.

Serum globulins that precipitate or gel on cooling at low temperatures (nominally 35°–4° C. and generally 25°–4° C.) and redissolve on warming may occur in a variety of disorders such as myeloma, kala-azar, macroglobinemia, malignant lymphoma, collagen diseases as lupus, glomerulonephritis, infectious mononucleosis, syphilis, cytomegalovirus disease, rheumatoid arthritis, and other autoimmune diseases. The globulins may represent homogeneous proteins that have become physically altered (myeloma), mixtures of immunoglobulins (as IgG and IgM), or immune complexes (such as antigen and antibody), possibly with complement (as in systemic lupus erythematosus). The term cryoglobulins refers to those abnormal globulins. The molecular weight of cryoglobulins vary from 100,000 to 1,800,000 daltons molecular weight. By taking advantage of the precipitation or gelling effect of cryoglobulins their removal can be effected. As the plasma is separated from blood it is cooled. While in some clinical situations only a small temperature change from physiological temperature of 37° C. is needed to start gelling or precipitation, in the clinical situations temperatures as low as near freezing for extended times are necessary to cause precipitation in collected serum.

Occasionally cryoglobulins will precipitate out at room temperature, but as a rule, sera have to be cooled to 10° C. or lower, before precipitation occurs. With the cryoglobulins cooled to a level to cause precipitation or gelling the filtration of these substances from the plasma is greatly facilitated. The advantage of this scheme over the direct filtration scheme without excessive cooling is that the membrane porosity or pore size may be increased allowing for higher sieving of the normal proteins in the plasma and therefore more efficient return to the patient. While cooling of the plasma would normally take place in the circuit the temperature decrease may not always be uniform or low enough therefore a heat exchange system would be most desirable to cool the plasma. To avoid chills to the patient or precipitation or gelling of the cryoglobulins in the blood circuit returning to the patient, the blood should be rewarmed by heater 30 to physiological temperature on its return to the patient.

EXPERIMENTAL STUDIES

EXPERIMENT #1

Asahi (Asahi Medical Co., Tokyo, Japan) S-type filter containing cellulose acetate hollow fiber membranes with a nominal pore size of 0.2 microns with 84% porosity was evaluated for sieving properties of $C_{1q}$ binding immune complexes that are present in rheumatoid arthritis. Plasma obtained by centrifugation from patient H.L. who had high values of $C_{1q}$ binding immune complexes was perfused through the S-type filter. Sieving coefficients (concentration of filtrate divided by the concentration in the fluid flow stream to the filter) for the $C_{1q}$ binding immune complexes averaged 0.49 over a two-hour perfusion period. This study demonstrated that these complexes can be filtered from plasma but that its efficiency is low, allowing only about 50% of the complexes to be removed. This would necessitate longer treatment time.

EXPERIMENT #2

Due to the relatively low efficiency of the Asahi S-type filter various available membranes of nominal pore size of 0.2 to 0.1 micron were selected for study. The membranes were Tuffryn HT-100 (polysulfone) with pore size of 0.1 micron from Gelman Sciences (Ann Arbor, Mich.), XM300 (acrylic copolymer) (approximately 0.02 micron pore size) from Amicon (Lexington, Mass), (VMWP-approximately 0.05 micron pore size) MF (mixed cellulose acetate and nitrate) from Millipore Corp. (Bedford, Mass.).

Plasma from a patient suffering from rheumatoid arthritis was procured by centrifugation. Such plasma contained elevated levels of rheumatoid factor and $C_{1q}$ binding immune complexes. The membranes were assembled into small test cells giving a total surface area of 56 cm². The plasma was recirculated through the test cells at ambient temperature. For testing the XM-300 membrane the plasma was filtered first through an Asahi filter. The filtration process reduces the concentration of macromolecules in the plasma. For one of the HT-100 membrane, in addition to first filtering the plasma through an Asahi filter, the plasma was used after decantation following refrigeration. This procedure results in the removal of a significant amount of cryoglobulins from the plasma. For the other HT-100 membrane tested and the MX 0.05 membrane tested the cryoprecipitates were resuspended in the plasma for the study. It is noted that for all membranes, complete sieving (no rejection) of small molecule weight solutes is achieved. Particularly noteworthy is the sieving of albumin. In the initial stages of the filtration studies (less than 30 minutes) nearly complete rejection (low sieving coefficient) was seen for the XM-300 membranes. There was about 27% rejection of $C_{lq}$ binding immune complexes and 32% rejection of rheumatoid factor for the HT-100 membrane at 10 minutes.

EXPERIMENT #3

A 54-year old white female was selected with extremely aggressive seropositive rheumatoid arthritis who failed all accepted modes of therapy and in addition failed cytotoxic drugs including Methotrexate and Cytoxan. The only therapeutic modality to which she has transiently responded has been plasmapheresis. The subject's blood was treated by the method and apparatus of FIG. 1, such treatment reducing her immune complex $C_{lq}$ Binding (<74 u/ml.) from 2256 units down to 688 units with a resultant improvement in symptomatology.

EXPERIMENT #4

Figure 3:
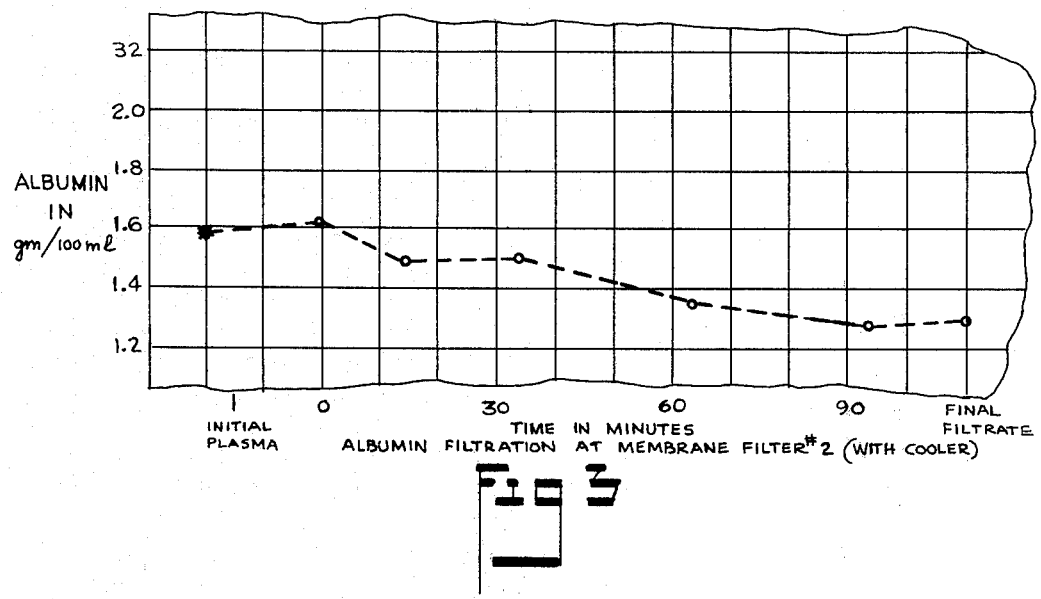
FIG. 3 is a chart showing albumin retention in a plasma solution filtered by the method and apparatus shown in FIG. 1.
Figure 4:
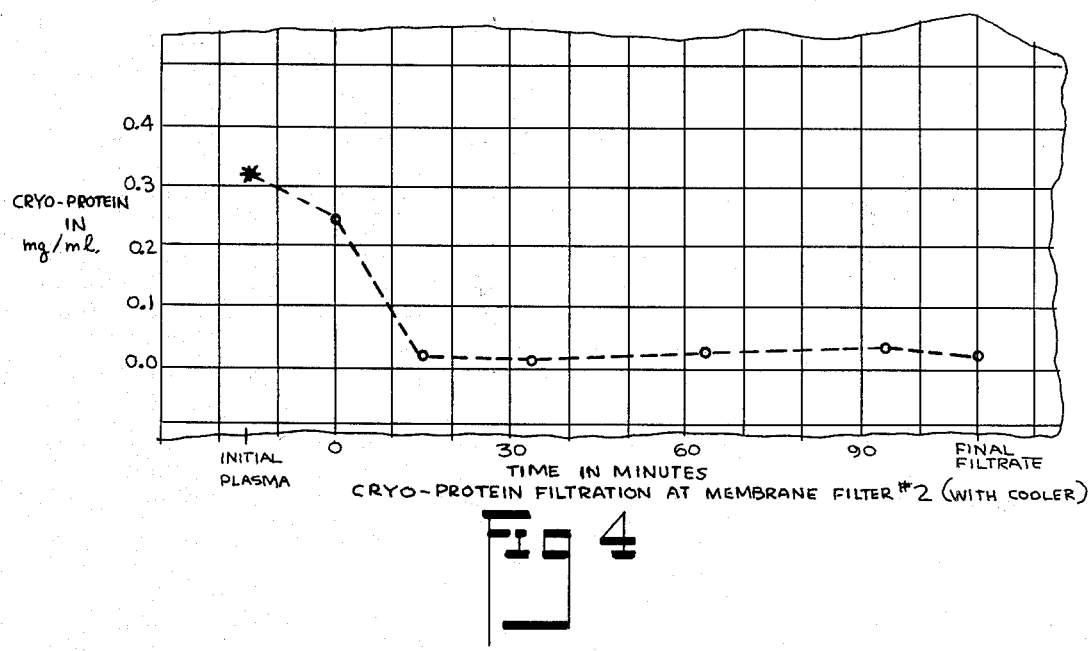
FIG. 4 is a chart showing the cryo-protein removal in the same plasma solution used in the FIG. 3 chart and employing the method and apparatus shown in FIG. 1.

Reference is now made to FIGS. 3 and 4. In this experiment, a patient's plasma was treated by the method and apparatus of FIG. 1. It will be noted in FIG. 3 that the albumin loss was only about 20%, while as shown in FIG. 5, the cryo-protein reduction was about 95%.

Both charts (FIGS. 3 and 4) are from the same single experiment, which was done under a cooled state. Such experiment shows that the albumin substantially remains in solution (which is highly desirable) and the cry-oprotein (which represents the macromolecules) are almost all removed from the plasma solution.

In the method and apparatus of FIG. 1, treatment time is normally about two to four hours, with roughly 1.7 to 3.0 liters of plasma being treated.

Controlled recirculation of the treated plasma from line 24 over to line 18 could be effected if desired.

Thus, the invention provides a method of removing macromolecules from a plasma solution including providing a plasma solution containing macromolecules including a minimum size thereof, cooling the plasma solution to a temperature not lower than just above the freezing point of the plasma solution, and filtering the plasma solution with a membrane filter 2 having a porosity up to said minimum size to remove macromolecules of predetermined size from the plasma solution.

Also provided is a method of removing macromolecules from a physiological solution such as blood including, securing a physiological solution from a patient, separating the physiological solution stream into a concentrated cellular element stream and a plasma stream containing macromolecules therein by either a membrane filter or a centrifuge, filtering macromolecules of predetermined size out of the plasma stream to form a filtered plasma stream, combining the filtered plasma stream and the cellular element stream to form a processed stream, and returning the processed stream to the patient in a continuous process. The step of heating the processed stream to approximately body temperature before it is returned to the patient may also be included.

In such method the membrane filter for removing the macromolecules out of the separated stream has a porosity of nominally 0.01 to 0.2 microns to pass macromolecules to approximately 70,000 molecular weight and below and reject or collect macromolecules of approximately 100,000 molecular weight and over.

The invention also contemplates an apparatus for removing macromolecules from a patient's physiological solution including, plasma separation means 1 for dividing a physiological solution such as blood containing macromolecules into a concentrated cellular element stream and a plasma stream, a cooler 20 in fluid flow communication with the plasma separation means 1 for receiving the plasma stream therefrom and cooling such plasma stream to cause the macromolecules therein to gel or precipitate, filter means 2 in fluid flow communication with the cooling unit 20 for receiving the cooled plasma stream therefrom and filtering such cooled plasma stream to remove macromolecules of a predetermined size therefrom, fluid flow communication means 26 for receiving the filtered plasma macrosolute stream from the filter means and for receiving the concentrated cellular element stream and combining said two last-named streams to form a processed stream for return to the patient in a continuous process.

Further included is a pump 12 in fluid flow communication with the plasma separation means 1 and with the patient to pump the physiological solution from the patient to the plasma separation means 1.

The cooling unit 20 cools the separated plasma stream to a temperature of between just above the freezing point of the separated plasma stream and approximately 35° centigrade, although it is to be understood that the cooler 20 may be eliminated in certain instances.

Also, the heater unit 30 is preferred, but may be eliminated if the temperature in the line 28 is near body temperature.

The terms and expressions which have been employed are used as terms of description, and not of limitation, and there is no intention, in the use of such terms and expressions, of excluding any equivalents of the features shown and described or portions thereof, but it is recognized that various modifications are possible within the scope of the invention claimed.

What is claimed is:

1. A method of removing macromolecules from a plasma solution comprising; providing a plasma solution containing macromolecules including a minimum size thereof, effecting predetermined cooling of said plasma solution to a temperature not lower than just above the freezing point of the plasma solution, and filtering said cooled plasma solution with a membrane filter having a porosity up to said minimum size to remove macromolecules of predetermined size from the plasma solution.

2. A method of removing macromolecules from a physiological solution comprising;

securing a physiological solution stream from a patient, separating said physiological solution stream into a concentrated cellular element stream and a plasma stream containing macromolecules including a size above substantially 100,000 daltons therein, filtering macromolecules of a size above substantially 100,000 daltons out of the plasma stream to form a filtered plasma stream substantially free of macromolecules of a size above substantially 100,000 daltons by flow of the plasma stream through a porous medium having openings of a size adapted to pass molecules of a size less than substantially 100,000 daltons and to retain macromolecules of a size above substantially 100,000 daltons, combining said filtered plasma stream and said cellular element stream to form a processed stream, and returning the processed stream to the patient.

3. The method of claim 2 and further including the step of heating the processed stream to approximately body temperature before it is returned to the patient.

4. A method of removing macromolecules from a physiological solution comprising;

securing a physiological solution stream from a patient, separating said physiological solution stream into a concentrated cellular element stream and a plasma stream containing macromolecules therein, effecting predetermined cooling of said plasma stream to a temperature of between just above the freezing point of the plasma stream and 35° centigrade, filtering macromolecules of predetermined size out of the cooled plasma stream to form a filtered plasma stream, combining said filtered plasma stream and said cellular element stream to form a processed stream, heating the processed stream to body temperature, and returning the heated processed stream to the patient.

5. The method of claim 4 wherein the separation of said physiological solution stream into a concentrated cellular element stream and a plasma stream is effected by a centrifuge.

6. The method of claim 4 wherein the separation of said physiological solution stream into a concentrated cellular element stream and a plasma stream is effected by a membrane filter, and further including the step of adding a complexing agent to the plasma stream before it is filtered to promote macromolecule formation.

7. The method of claim 4 wherein said physiological solution is blood.

8. The method of claim 4 wherein said physiological solution is lymph or ascitic fluid.

9. A method of removing macromolecules from a stream of physiological solution removed directly from a patient including; forming from a stream of a patient's physiological solution a separated stream containing macromolecules including a size above substantially 100,000 daltons and substantially free of red blood cells, then using a membrane filter having a porosity to remove macromolecules of a size above substantially 100,000 daltons out of said separated stream by flow of the separated stream through a porous medium having openings of a size adapted to pass molecules of a size less than substantially 100,000 daltons and to retain macromolecules of a size above substantially 100,000 daltons, and then returning the filtered separated stream substantially free of macromolecules of a size above substantially 100,000 daltons to the patient.

10. The method of claim 9 and further including the step of pumping the physiological solution from the patient before it is formed into a separated stream.

11. A method as defined in claim 9 wherein said stream of physiological solution is blood, and said separated stream is plasma which includes said macromolecules.

12. A method as defined in claim 11, wherein the step of forming a separated stream removes macromolecules from below 0.2 microns effective diameter.

13. A method as defined in claim 12 wherein the step of forming a separated stream is effected with a porous membrane having a nominal pore size of 0.2 to 1.0 micron when filtering plasma from blood.

14. A method as defined in claim 13 wherein the process is continuous.

15. A method of removing macromolecules from a stream of physiological solution removed directly from a patient including; forming from a stream of a patient's physiological solution a separated stream containing macromolecules, then using a membrane filter having a porosity to remove macromolecules of predetermined size out of said separated stream, and then returning the filtered separated stream substantially free of macromolecules of said predetermined size to the patient, and further including the step of adding a complexing agent to the separated stream before it is filtered by the membrane filter, said method being continuous.

16. A method of removing macromolecules from a stream of physiological solution removed directly from a patient including; forming from a stream of a patient's physiological solution a separated stream containing macromolecules, then using a membrane filter having a porosity to remove macromolecules of predetermined size out of said separated stream, then returning the filtered separated stream substantially free of macromolecules of said predetermined size to the patient, said stream of physiological solution being blood, and said separated stream being plasma which includes said macromolecules, and further including after the step of forming a separated stream containing said macromolecules and before using the membrane filter the step of cooling said separated stream to a temperature between about just above the freezing point of the separated stream and about 35° C. to cause such macromolecules to gel or precipitate.

17. A method of removing macromolecules from a stream of physiological solution removed directly from a patient including; forming from a stream of a patient's physiological solution, a separated stream containing macromolecules, then using a membrane filter having a porosity to remove macromolecules of predetermined size out of said separated stream, and then returning the filtered separated stream substantially free of macromolecules of said predetermined size to the patient, said membrane filter for removing the macromolecules out of the separated stream having a minimal porosity of nominally 0.01 to 0.2 microns to pass macromolecules of approximately 70,000 molecular weight and below and reject or collect macromolecules of approximately 100,000 molecular weight and over.

18. An apparatus for removing macromolecules from a patient's physiological solution comprising; plasma separation means for dividing a physiological solution containing macromolecules into a concentrated cellular element stream and a plasma stream, a cooler in fluid flow communication with said plasma separation means for receiving the plasma stream therefrom and cooling such plasma stream to a predetermined temperature to cause the macromolecules therein to gel or precipitate, filter means in fluid flow communication with said cooling unit for receiving the cooled plasma stream therefrom and filtering such cooled plasma stream to remove macromolecules of a predetermined size therefrom, fluid flow communication means for receiving the filtered plasma stream from the filter means and for receiving the concentrated cellular element stream and combining said two last-named streams to form a processed stream for return to the patient.

19. The structure of claim 18 and further including a pump in fluid flow communication with the plasma separation means and with the patient to pump the physiological solution from the patient to the plasma separation means.

20. The structure of claim 19 wherein a complexing agent is added to the plasma stream before it is filtered by the filter means to promote macromolecule formation.

21. The structure of claim 18 wherein said physiological solution is blood.

22. The structure of claim 21 wherein the separated plasma stream is blood plasma containing macromolecules.

23. The structure of claim 18 wherein the physiological solution is lymph or ascitic fluid.

24. The structure of claim 18 wherein said cooling unit cools the separated plasma stream to a temperature of between just above the freezing point of the separated plasma stream and approximately 35° centigrade.

25. The structure of claim 18 wherein said plasma separation means is a centrifuge.

26. The structure of claim 18 wherein said plasma separation means is a membrane filter.

27. The structure of claim 18 and further including a heater unit operatively secured to the fluid flow communication means at a point in such fluid flow communication means after said two last-named streams are combined to heat the processed stream to approximately body temperature before it is returned to the patient.

28. An apparatus for removing macromolecules from a patient's physiological solution comprising; plasma separation means for dividing a physiological solution containing macromolecules into a concentrated cellular element stream and a plasma stream, a cooler in fluid flow communication with said plasma separation means for receiving the plasma stream therefrom and cooling such plasma stream to a predetermined temperature to cause the macromolecules therein to gel or precipitate, filter means in fluid flow communication with and encased in said cooling unit for receiving the cooled plasma stream therefrom and filtering and further cooling such cooled plasma stream to remove macromolecules of a predetermined size therefrom, fluid flow communication means for receiving the filtered plasma stream from the filter means and for receiving the concentrated cellular element stream and combining said two last-named streams to form a processed stream substantially free of macromolecules of said predetermined size for return to the patient.

29. The structure of claim 28 wherein the cooler cools the plasma stream to a temperature of between just above the freezing point of the plasma stream and approximately 35° centigrade.

30. The structure of claim 28 and further including a heater unit operatively secured to the fluid flow communication means at a point in such fluid flow communication means after said two last-named streams are combined to heat the processed stream to approximately body temperature before it is returned to the patient.

31. An apparatus for removing macromolecules from a patient's physiological solution comprising; separation means for dividing a physiological solution containing macromolecules into a concentrated cellular element stream and a plasma stream, filter means in fluid flow communication with said plasma separation means for receiving the plasma stream therefrom and filtering such plasma stream to remove macromolecules of a size above substantially 100,000 daltons therefrom by flow of the plasma stream through said filter means which has openings of a size adapted to pass molecules of a size less than substantially 100,000 daltons and to retain macromolecules of a size above substantially 100,000 daltons, fluid flow communication means for receiving the filtered plasma stream from the filter means and for receiving the concentrated cellular element stream and combining said two last-named streams to form a processed stream substantially free of macromolecules of a size above substantially 100,000 daltons for return to the patient.

32. An apparatus for removing macromolecules from a patient's physiological solution comprising; plasma separation means for dividing a physiological solution containing macromolecules into a concentrated cellular element stream and a plasma stream, filter means in fluid flow communication with said plasma separation means for receiving the plasma stream therefrom and filtering such plasma stream to remove macromolecules of a predetermined size therefrom, fluid flow communication means for receiving the filtered plasma stream from the filter means and for receiving the concentrated cellular element stream and combining said two last-named streams to form a processed stream substantially free of macromolecules of said predetermined size for return to the patient, a complexing agent being added to the plasma stream before it is filtered by the filter means to promote macromolecule formation.

* * * * *